United States Patent [19]

Fenton

[11] 4,329,429
[45] May 11, 1982

[54] LACTASE PREPARATION

[75] Inventor: Dennis M. Fenton, Gales Ferry, Conn.

[73] Assignee: Pfizer Inc., New York, N.Y.

[21] Appl. No.: 133,036

[22] Filed: Mar. 24, 1980

[51] Int. Cl.$^3$ .............................................. C12N 9/38
[52] U.S. Cl. .................................. 435/207; 435/814; 435/911; 435/921
[58] Field of Search .................... 435/207, 814, 816

[56] References Cited

U.S. PATENT DOCUMENTS

| | | | |
|---|---|---|---|
| 2,715,601 | 8/1955 | Morgan | 435/207 |
| 3,592,739 | 7/1971 | Sternberg | 435/207 |
| 3,885,050 | 5/1975 | Ridgway et al. | 426/60 |
| 3,961,080 | 6/1976 | Sugimoto et al. | 426/60 |
| 4,235,970 | 11/1980 | Leach et al. | 435/202 |

OTHER PUBLICATIONS

Yasumatsu et al., Agr. Biol. Chem.; vol. 29, No. 7, pp. 665 to 671, (1965).

Primary Examiner—Lionel M. Shapiro
Attorney, Agent, or Firm—Charles J. Knuth; Peter C. Richardson

[57] ABSTRACT

A process for the release of lactase from yeast cells comprising contacting the cells with an alkyl alcohol or a dialkyl ketone, followed by extraction of the lactase in an aqueous solution at a pH in the range 5.5 to 8.0 is disclosed. Also disclosed is a process for the selective reduction of protease activity in lactase preparations comprising heating an aqueous solution of lactase containing protease impurities in the presence of glycerol. Lactase stability during the heating process can optionally be enhanced by addition of manganous ion.

18 Claims, No Drawings

LACTASE PREPARATION

BACKGROUND OF THE INVENTION

This invention relates to the preparation and purification of lactase.

Lactase, or beta-galactosidase, is an enzyme effective for the hydrolysis of lactose to glucose and galactose. Accordingly, lactase is useful in the dairy industry, for example in cheese making, where the addition of lactase to the cheese milk increases the rate of lactose hydrolysis and thereby shortens cheese ripening times, increases production capability and allows production of improved products. Lactase is also useful for administration to persons who are physiologically intolerant to lactose.

Lactase is an intracellular constituent of certain microorganisms which are readily produced by conventional fermentation methods, including for example microorganisms of the genus Kluyveromyces, previously considered as Saccharomyces, especially *Kluyveromyces fragilis* and *Kluyveromyces lactis*, and other yeasts such as those of the genera Candida, Torula and Torulopis, and the like. In the past, cells of such microorganisms have been cultivated in a suitable nutrient medium, harvested and dried, whereafter the whole dried cells are used to impart lactase activity in the desired application. This method is undesirable in that the other cell constituents are also added to the cheese milk and can impart undesirable taste and odor characteristics. Prior art methods to overcome this problem have involved methods of releasing the lactase from the interior of the cells, especially by breaking the cell walls by mechanical homogenization, grinding or chemical means. However, these methods generally require long processing times, are expensive and will release not only lactase but other intracellular enzymes and proteins, and their degration products, from which the lactase must desirably be separated. In this regard, one particular problem has been that in the release of intracellular lactase from microorganism cells, the enzyme protease is also released and it has been difficult to remove the protease activity from the lactase preparation. When protease is present in the lactase preparation added to cheese milk to accelerate cheese ripening, undesirable bitter off-flavors, attributed to peptide formation by proteolytic degradation of milk proteins, may be produced. Accordingly, in view of the above there has been a need for improved processes for the release of lactase from microorganisms and there has further been a need for processes for the purification of lactase preparations so obtained, especially for processes to selectively remove protease activity from lactase preparations.

SUMMARY OF THE INVENTION

In one aspect, the present invention provides an improved process for the release of lactase from lactase-containing yeast cells in good yield and purity in relatively short reaction times. The process comprises: (a) Contacting lactase-containing yeast cells with from about 20 weight percent to 95 weight percent of a compound selected from alkyl alcohols of 1 to 4 carbon atoms and dialkyl ketones having from 1 to 4 carbon atoms in each alkyl group, based on the total weight of said cells and alcohol or ketone, at a temperature from about 5° C. to 35° C., preferably at 20° C. to 30° C.; and then (b) Contacting the alcohol- or ketone-treated cells with an aqueous solution having a pH from about 5.5 to 8.0, preferably about 6.4 to 7.0, at a temperature from about 5° C. to 35° C., preferably about 20° C. to 30° C. Preferred compounds for use in step (a) are methanol, ethanol and isopropanol or mixtures thereof, most preferably ethanol. Preferably, the alcohol or ketone is used in an amount from about 60 to 90 weight percent. Preferred yeast cells for use in the present process are those of the genera Kluveromyces, Candida and Torula. Preferred species include *Kluveromyces fragilis*, *Kluyveromyces lactis* and *Torula cremoris*, also known as *Candida pseudotropicalis*.

In another aspect, the present invention provides a process for selectively reducing protease activity in a protease-containing lactase preparation comprising heating an aqueous solution containing the lactase preparation and from about 30 weight percent to 90 weight percent, preferably from 40 weight percent to 60 weight percent, of glycerol, based on the total weight of the water-glycerol solution, at a temperature from about 35° C. to 60° C., preferably from 45° C. to 55° C., at a pH from about 5.5 to 8.0, preferably 6.4 to 7.0, until the protease activity is substantially reduced. If desired, manganous ion can be added to the aqueous-glycerol solution in a concentration from about $10^{-4}$ to $10^{-2}$ M to enhance stability of the lactase during the heating process.

DETAILED DESCRIPTION OF THE INVENTION

The process of the present invention can be utilized to release lactase from lactase-containing yeast cells well known in the art. Suitable microorganisms include those of the genus Kluyveromyces, especially *Kluyveromyces fragilis*, many strains of which are publicly available from culture collections, for example *Kluyveromyces fragilis* ATCC 10022, ATCC 8608, ATCC 8582, ATCC 12424 and also *Kluyveromyces lactis*. Other microorganisms from which lactase can be released by use of the present process include those of the genera Candida and Torula, especially *Torula cremoris*, a strain of which is publicly available from the University of California at Davis, California, Culture No. UCD55-31, and the like. Preferred yeast cells for use in the present process are those of the genus Kluyveromyces, especially those of the species *Kluyveromyces fragilis* and *Kluyveromyces lactis*, and *Torula cremoris*, also known as *Candida pseudotropicalis*. It will be understood that mutants of these known and publically available microorganisms, prepared by conventional techniques such as irradiation with X-rays or ultraviolet light, treatment with nitrogen mustards or the like, will also be suitable for use in the present process.

The lactase-containing yeast cells are generally obtained by aerobic cultivation in a suitable nutrient medium, for example in an aqueous medium containing lactose, including media containing whey, together with sources of phosphorus, nitrogen and potassium, for example ammonium phosphate, potassium phosphate and similar salts. Such nutrient media are well known to those skilled in the art.

Using conventional fermentation methods known in the art the yeast cells are cultivated until a sufficient concentration of cells in the nutrient medium has been obtained, for example by conducting the fermentation in the nutrient medium at a temperature from about 20° C. to 35° C., preferably from 25° C. to 30° C. for a period of about 48 to 100 hours. The cells are then harvested, for example by filtration or centrifugation.

In order to release the intracellular lactase the yeast cells are first contacted with an alkyl alcohol of 1 to 4 carbon atoms or a dialkyl ketone having 1 to 4 carbon atoms in each alkyl group at a temperature from 5° C. to 35° C., preferably from 20° C. to 30° C. The alcohol or ketone is employed in an amount from about 20 weight percent to about 95 weight percent, preferably from 60 weight percent to 90 weight percent, based of the total weight of cells and alcohol or ketone. The cells are contacted with the alcohol or ketone for a period of about 2 minutes to about 20 hours, preferably 30 minutes to 2 hours. The alcohol or ketone is then preferably removed from the cells, for example by filtration of the cells, evaporation of the solvent, freeze drying or the like. However, when the alcohol or ketone is used in an amount less then about 75 weight percent to 80 weight percent, removal of the alcohol or ketone is not essential and the cells can be treated in the subsequent step of the process with an aqueous solution at a pH from about 5.5 to 8.0 in the presence of the alcohol or ketone.

It should be appreciated that the treatment of the cells with an alkyl alcohol or dialkyl ketone, in accord with the process of this invention, is not a solvent extraction of the intracellular lactase by the alcohol or ketone. Little or no lactase is extracted from the cell by the alcohol or ketone under the conditions of the present process. While not wishing to be bound by any particular theory of the mechanism of the present process, it is believed that the alcohol or ketone acts to make the cell wall more permeable and to allow the release of the intracellular lactase when the cells are subsequently suspended in an aqueous solution at a pH of about 5.5 to 8.0, as described in more detail hereinafter.

After treatment with the alcohol or ketone, as described above, the alcohol- or ketone-treated cells are suspended in an aqueous solution having a pH from about 5.5 to 8.0, preferably from about 6.4 to 7.0, most preferably at about 6.6, preferably by employing an appropriate buffer solution, for example a 0.1 M sodium or potassium phosphate solution, or a 0.1 M citrate—phosphate solution, or the like. Preferably, the solution is agitated, for example by stirring or shaking, to promote release of the lactase. The solution is maintained at a temperature from about 5° C. to 35° C., preferably from 20° C. to 30° C. The cell concentration in the aqueous solution is not critical, but is preferably in the range from about 10 to 80 grams per liter, preferably about 30 to 50 grams per liter. The cells are suspended in the aqueous solution, preferably a 0.1 M sodium or potassium phosphate buffer solution, for periods of about 1 to 20 hours, with times of about 10 to 20 hours being optimum for maximum yields of extracted lactase. If times longer than about 20 hours are employed, some loss in the yield of released lactase may be experienced due to microbial degradation of the enzyme, although such losses may be minimized by operating under sterile conditions or by addition of a preservative. Lactase is released from the cells into the aqueous solution, together with amounts of other intracellular enzymes or proteins, including protease, although the extraction of the undesired components is substantially less than by prior art methods of releasing lactase, for example by homogenization or mechanical grinding of the cells to mechanically rupture the cell walls.

The amount of lactase released from the cells is measured in terms of lactase units, as is conventional in the art. Thus, for the purposes of this invention, lactase units are determined by the rate of degradation of o-nitro-phenyl-beta-D-galactopyranoside (ONPG) to o-nitro-phenyl (ONP) and D-galactopyranoside, see for example Wendorf et al, J. Milk Food Tech. 34, 451 (1971). More specifically, for the purposes of the present specification, the rate of degradation of ONPG is determined by measuring with a spectrophotometer the absorption at 420 nm in a solution prepared by mixing 7 ml of 0.1 M potassium phosphate buffer solution containing 0.1% bovine serum albumin, 1 ml of a $10^{-3}$ M solution of manganous sulfate monohydrate, 2 ml of a 0.02 M solution of ONPG and 1 ml of the lactase-containing solution to be tested. The assay is run for 20 minutes at 37° C. and the reaction is then stopped by the addition of 1 ml of 2 M ammonium hydroxide containing $2 \times 10^{-3}$ M disodium EDTA. The number of lactase units is then determined by the change in absorption at 420 nm, one lactase unit being equal to one micromole of ONP produced per minute. Similarly, the amount of protease in solution is expressed as protease units, measured, for the purposes of the present specification, as the rate of degradation of azocoll, a dyed collagen polymer, see for example Heym, Arch. Biochem. Biophys. 127, 89 (1962). More specifically, for the purposes of the present specification, the rate of degradation of azocoll has been determined by measuring the change in absorption at 520 nm using a spectrophotometer, in a solution prepared by mixing 3 ml of a 0.1 M sodium phosphate buffer solution, 10 mg of azocoll and 1 ml of the protease-containing solution to be tested. The solution is incubated for 30 minutes at 37° C. with shaking and the reaction is then stopped by filtration of the residual azocoll. The number of protease units is then determined from the change in absorption at 520 nm per minute.

Following the release of the lactase, together with lesser amounts of protease and other proteins, from the yeast cells into the aqueous extraction medium, the residual solid cell materials are removed, for example by filtration, to provide an aqueous lactase preparation comprising a solution of lactase together with lesser amounts of protease impurities. If desired, the lactase can be isolated from this solution by conventional means, for example by freeze drying or by addition of a non-solvent, such as acetone, to precipitate the lactase, addition of sucrose followed by spray drying, and the like. However, it will be understood that lactase isolated from the aqueous extraction medium of the present process by these means will contain protease impurities, which will contribute to undesirable flavor and taste characteristics when the lactase preparation is employed in cheese making. Accordingly, it is preferred that the lactase obtained from yeast cells by the process of the present invention, as described above, be purified to remove the protease activity.

In accord with a second aspect of the present invention, such protease activity can be removed from lactase preparations by heating an aqueous solution of the lactase preparation containing protease impurities with from about 30 to 90 weight percent of glycerol, based on the total weight of the water-glycerol solution, at a temperature from about 35° C. to 60° C. at a pH from about 5.5 to 8.0. It will therefore be apparent that the aqueous solution containing the released lactase and protease impurities obtained by extraction of the alcohol- or ketone-treated yeast cells, in accord with the present invention, can be purified directly by the addition of glycerol and heating, without the need to isolate the lactase from the aqueous extraction medium. Lactase concentrations in the aqueous-glycerol solution of the purification process are not critical, but are generally in the range of about 1,000 to 25,000 lactase units per ml, preferably about 2000 to 25,000 units/ml. Preferably therefore, the aqueous lactase containing solution obtained by the previously described extraction process of alcohol- or ketone-treated cells, is concentrated to provide a suitable lactase concentration prior to the addition of the glycerol thereto.

The purification process is preferably conducted at a temperature from about 45° C. to 55° C., preferably at a pH in the range 6.4 to 7.0, most preferably about 6.6, where the lactase is most stable. Lactase stability in the purification process may be further enhanced, if desired, by the addition to the solution of a soluble divalent manganese salt, for example manganous sulfate, manganous chloride, manganous nitrate and the like, in an amount sufficient to provide a manganous iron concentration from about $10^{-4}$ to $10^{-2}$ M.

The lactase containing aqueous-glycerol solution is heated until the protease activity is substantially reduced. The time required will depend on the reaction temperature, but will generally be from about 3 hours at 60° C. to about 10 days at 35° C., with optimum times of about 6 to 12 hours at a temperature of 50° C. Under the conditions of the process, the protease impurities are rapidly denatured and the protease activity can be reduced to 10% or less of the initial value by the present process. By contrast, the lactase is selectively stabilized by the glycerol, and by manganous ion, if added, and greater than 90% of the initial lactase activity is retained. During the heating process, a precipitate of denatured protein, including denatured protease, is formed and is removed from the solution, for example by filtration, to provide a purified solution of the desired lactase. The lactase can then be isolated from the solution, if desired, by conventional methods known in the art.

It will be understood that the above described purification process for the selective reduction of protease activity from lactase preparations by heating in the presence of glycerol is particularly suitable for the purification of lactase obtained by the treatment of yeast cells with an alcohol or ketone, followed by extraction in an aqueous solution at a pH from about 5.5 to 8.0, in accord with the present invention. However, this process for selectively reducing protease activity can also be employed to remove or reduce protease activity in lactase preparations obtained by other processes, for example, by the prior art methods of mechanical grinding or homogenization and the purification of such lactase preparations is within the scope of the present invetion.

The present invention is illustrated by the following examples. However, it will be understood that the invention is not limited to the specific details of these examples.

EXAMPLE 1

An inoculum of *Torula cremoris* (*Candida pseudotropicalis*) obtained from the University of California at Davis, California, Culture No. UCD 55-31, was prepared by cultivating the cells for 12 hours at 28° C. in 1 liter of a nutrient medium of the following composition:

| | |
|---|---|
| Whey | 40.0 g/l |
| (NH$_4$)$_2$SO$_4$ | 5.0 g/l |
| K$_2$HPO$_4$ | 5.0 g/l |
| Corn Steep Liquor | 1.0 g/l |
| MgSO$_4$ . 7H$_2$O | 0.5 g/l | the pH of which was adjusted to 4.5 with sulfuric acid and the medium autoclaved at 110° C. for 45 minutes.

A 14 liter fermentor containing 8.0 liters of a medium of the following composition:

| | |
|---|---|
| KH$_2$PO$_4$ | 1.8 g/l |
| NH$_4$H$_2$PO$_4$ | 1.0 g/l |
| (NH$_4$)$_2$HPO$_4$ | 1.0 g/l |
| MgSO$_4$ . 7H$_2$O | 0.1 g/l |
| FeSO$_4$ 7H$_2$O | 5.0 mg/l |
| MnSO$_4$ . 7H$_2$O | 5.0 mg/l | which had been autoclaved for 30 minutes at 121° C., was inoculated (10% v/v) with the above inoculum.

A feed (2.6 liters) of the following composition:

| | |
|---|---|
| Lactose | 363 g/l |
| Yeast Extract | 6.0 g/l |
| Corn Steep Liquor | 3.0 g/l |
| Nicotinic Acid | 6.0 mg/l | which had been autoclaved 45 minutes at 110° C., was added continuously over the 60 hour fermentation.

Dissolved oxygen was maintained above 10% during the fermentation with aeration and agitation increasing from 0.5 vol/vol/min to 0.75 vol/vol/min and 310 RPM to 380 RPM, respectively. Fermentation temperature was 30° C. and pH was maintained at 4.5.

After a period of 60 hours the cell concentration was 18 g/l and the lactase content of the cells was measured as 4200 units/gram. The lactase-rich cells were harvested by filtration.

The yeast cell paste, containing 1.8 grams of cells, obtained from the fermentation broth was treated with 6.3 grams of ethanol. After a period of 90 minutes the ethanol was removed by filtration and the cells were resuspended in 0.1 M potassium phosphate buffer, pH 6.6. The cell concentration in this buffer was adjusted to approximately 40 g/l. Lactase release was attained by agitating the ethanol-treated cells in the extraction buffer for a period of 15 hours. The extracted cells were then removed by filtration from the lactase-enriched buffer. The final enzyme solution contained approximately 6 mg/ml protein and 65 units/ml of lactase activity, representing a yield of about 45%, based on the intracellular lactase content of the harvested cells.

EXAMPLE 2

The procedure of Example 1 was repeated on further batches of the harvested cells of Example 1 using different alcohols and ketones in place of ethanol for treatment of the cells. The results obtained were as follows:

| Compound | % Yield | Lactase Activity (Units/ml) |
|---|---|---|
| Methanol | 45 | 66 |
| Isopropanol | 37 | 52 |
| Butanol | 1 | 1.5 |
| T-butanol | 45 | 66 |

| Compound | % Yield | Lactase Activity (Units/ml) |
|---|---|---|
| Acetone | 10 | 13 |
| Methyl Ethyl Ketone | 10 | 13 |
| Methyl Isobutyl Ketone | 7.5 | 10 |

EXAMPLE 3

The release of lactase by treatment of cells with ethanol followed by extraction with 0.1 M sodium phosphate buffer solution, in accord with the procedure described in Example 1, was demonstrated for strains of *Kluyveromyces fragilis*. The cells were cultivated for 24 hours in 1 liter of the inoculum medium of Example 1 in a 2 liter flask at 30° C. and were then collected by filtration. The amount of lactase released from approximately 1.5 grams of the cells by treatment with ethanol and extraction in 0.1 M potassium phosphate buffer following the procedure of Example 1 was as follows:

| Microorganism | Lactase Units/ml |
|---|---|
| *K. fragilis* ATCC 8608 | 5.0 |
| *K. fragilis* ATCC 8582 | 1.5 |
| *K. fragilis* ATCC 1022 | 1.5 |
| *K. fragilis* ATCC 12424 | 2.0 |

EXAMPLE 4

Three liters of a 1:1 glycerol:0.1 M potassium phosphate solution, pH 6.6, containing 3000 units/ml of lactase and 0.24 protease units/ml and containing $10^{-3}$ M manganous ion, added as manganous sulfate, was heated at 50° C. for 6 hours. A white precipitate of denatured protein formed during the heating and was filtered off. The protease activity remaining in the solution was 0.3 units/ml, representing the removal of about 90% of the original protease activity. By contrast, the lactase activity of the resulting solution was measured as 2,760 units/ml, representing the retention of over 90% of the initial lactase activity.

EXAMPLE 5

The procedure of Example 4 was repeated but using a temperature of 37° C. rather than 50° C. After 9 days of heating approximately 90% of the initial protease activity was removed while about 95% (2850 units/ml) of the initial lactase activity was retained.

We claim:

1. A process for the release of lactase from lactase-containing yeast cells comprising the steps of (a) contacting said cells with from about 20 weight % to 95 weight % of a compound selected from alkyl alcohols of 1 to 4 carbon atoms and dialkyl ketones having from 1 to 4 carbon atoms in each alkyl group, based on the total weight of said cells and said compound, at a temperature from 5° C. to 35° C., and then (b) contacting said cells with an aqueous solution having a pH from about 5.5 to 8.0 at a temperature from about 5° C. to 35° C. and separating the cells from the resulting lactase-containing solution.

2. A process according to claim 1 wherein said cells are of the genera Kluyveromyces, Candida, or Torula.

3. A process according to claim 2 wherein the temperature of each of steps (a) and (b) is from about 20° C. to 30° C.

4. A process according to claim 2 wherein the pH of said aqueous solution is from 6.4 to 7.0.

5. A process according to claim 2 wherein the compound of step (a) is methanol, ethanol, isopropanol or mixtures thereof.

6. A process according to claim 5 wherein said compound is ethanol.

7. A process according to claim 5 wherein the amount of the compound of step (a) is 60 weight % to 90 weight %.

8. A process according to claim 2 wherein said cells are separated from said compound after step (a).

9. A process according to claim 6 wherein the temperature of each of steps (a) and (b) is from 20° C. to 30° C. and the aqueous solution of step (b) is selected from about 0.1 M potassium phosphate buffer and about 0.1 M sodium phosphate buffer.

10. A process according to claim 9 wherein said cells are of the species *Kluyveromyces fragilis*.

11. A process according to claim 9 wherein said cells are of the species *Kluyveromyces lactis*.

12. A process according to claim 9 wherein said cells are of the species *Torula cremoris*.

13. A process according to claim 1 comprising the additional step of heating an aqueous solution of said released lactase and from about 30 to 90 weight % glycerol, based on the total weight of said solution, at a temperature from about 35° C. to about 60° C. at a pH from about 5.5 to 8.0 until the protease activity in said solution is substantially reduced.

14. A process for selectively reducing protease activity from a protease-containing lactase preparation comprising heating an aqueous solution containing said preparation and from about 30 to 90 weight percent glycerol, based on the total weight of said solution, at a temperature from about 35° C. to about 60° C. at a pH from about 5.5 to 8 until said protease activity is substantially reduced.

15. A process according to claim 14 wherein the temperature is from about 45° C. to about 55° C.

16. A process according to claim 14 wherein the glycerol concentration in said solution is from about 40 to 60 weight percent.

17. A process according to claim 14 wherein the pH is from about 6.4 to 7.0.

18. A process according to claim 14 wherein said solution contains manganous ion in a concentration from about $10^{-4}$ to $10^{-2}$ Molar.

* * * * *